(12) United States Patent
Seida et al.

(10) Patent No.: US 9,587,935 B2
(45) Date of Patent: Mar. 7, 2017

(54) METHOD AND DEVICE FOR DETECTING AND ANALYZING DEPOSITS

(71) Applicant: ASHLAND LICENSING AND INTELLECTUAL PROPERTY LLC, Dublin, OH (US)

(72) Inventors: Frank Seida, Werne (DE); Christian Flocken, Krefeld (DE); Patric Bierganns, Krefeld (DE); Michael Schultz, Bad Durrenbert (DE)

(73) Assignee: Solenis Technologies, LP (CH)

( * ) Notice: Subject to any disclaimer, the term of this patent is extended or adjusted under 35 U.S.C. 154(b) by 244 days.

(21) Appl. No.: 14/367,262

(22) PCT Filed: Dec. 20, 2012

(86) PCT No.: PCT/EP2012/076313
§ 371 (c)(1),
(2) Date: Jun. 20, 2014

(87) PCT Pub. No.: WO2013/092819
PCT Pub. Date: Jun. 27, 2013

(65) Prior Publication Data
US 2015/0000406 A1    Jan. 1, 2015

(30) Foreign Application Priority Data
Dec. 22, 2011 (EP) .................................... 11010109

(51) Int. Cl.
*G01N 29/024* (2006.01)
*G01B 17/02* (2006.01)
(Continued)

(52) U.S. Cl.
CPC ............. *G01B 17/02* (2013.01); *G01N 29/07* (2013.01); *G01N 29/44* (2013.01);
(Continued)

(58) Field of Classification Search
CPC ........ G01B 17/02; G01N 29/07; G01N 29/04; G01N 29/024; G01N 29/222;
(Continued)

(56) References Cited

U.S. PATENT DOCUMENTS 4,669,310 A * 6/1987 Lester .................. G01B 17/025
73/1.81
6,161,435 A 12/2000 Bond et al.
(Continued)

FOREIGN PATENT DOCUMENTS

DE       4318445      12/1994
EP       1816107       8/2007
WO      2009141135    11/2009

OTHER PUBLICATIONS

International Search Report, PCT/EP2012/076313, pp. 1-2, Jul. 9, 2013.

*Primary Examiner* — Laura Martin
*Assistant Examiner* — Rose M Miller
(74) *Attorney, Agent, or Firm* — Joanne Rossi; Michael Herman (57) ABSTRACT

The present invention relates to a method and device for detecting and analyzing deposits in liquid-bearing systems. More particularly, the device relates to being able to detect and analyze deposits in a liquid-bearing systems such as industrial plants that use and store fluids. The method relates to being able to determine a distribution of the run time of a detected ultrasonic reflection signal and analyzing the distribution to determine if deposits are deposited onto a reflecting area.

17 Claims, 4 Drawing Sheets (51) Int. Cl.
*G01N 29/44* (2006.01)
*G01N 29/07* (2006.01)

(52) U.S. Cl.
CPC ........... *G01N 2291/0237* (2013.01); *G01N 2291/0289* (2013.01); *G01N 2291/02854* (2013.01); *G01N 2291/044* (2013.01); *G01N 2291/045* (2013.01); *G01N 2291/101* (2013.01)

(58) Field of Classification Search
CPC . G01N 2291/0237; G01N 2291/02854; G01N 2291/0289; G01N 2291/044; G01N 2291/045; G01N 2291/101
USPC .................................. 73/597, 598, 627, 629
See application file for complete search history.

(56) References Cited

U.S. PATENT DOCUMENTS

| | | |
|---|---|---|
| 6,973,842 B1 | 12/2005 | Feller |
| 2007/0006656 A1 | 1/2007 | Batzinger et al. |
| 2013/0238133 A1* | 9/2013 | Greenberg ........... G01N 29/032 700/266 |
| 2014/0254323 A1* | 9/2014 | Sim ...................... G01N 29/032 367/87 |

* cited by examiner

Fig. 1

Fig. 2  TIME

METHOD AND DEVICE FOR DETECTING AND ANALYZING DEPOSITS

BACKGROUND

The present invention relates to a method and a device for detecting and analyzing deposits in liquid-bearing systems.

Industrial plants, like power plants, steel mills, pulp making plants or paper making plants, usually comprise means for conducting or storing fluids, e.g. pipe lines or fluid containers. It is a known issue that organic and inorganic matter deposits on the inner walls of these means for conducting or storing fluids, whereby an accumulation of deposits, like e.g. fouling or scaling, at least partially blocks the flow through the conducting means and conducted or stored fluids may become contaminated. This is an unwanted occurrence that causes a number of operational problems such as plugging of equipment, inefficient usage of chemicals, increased utility costs, lost production due to downtime, corrosion, and downgraded products from increased dirt counts.

In principle but not limited to, one can distinguish between fouling deposits on the one hand and scaling deposits on the other hand. Fouling deposits are organic deposits which often occur in the form of biofilms in aqueous systems. Such biofilms substantially consist of micro-organisms, e.g. bacteria, algae, fungi and protozoa. Contrary thereto, scale depositions occur from inorganic matter that have been identified include e.g. complexes of calcium (carbonate, oxalate, sulfate, silicates), aluminum (silicates, hydroxides, phosphates), barium sulfate, radioactive radium sulfate, and silicates of magnesium.

In order to avoid the accumulation of fouling deposits and in particular the growth of biofilms, biocides are added into the fluid concerned. Scaling deposits can be removed by adding chemical deposit control agents based on homopolymers, copolymers and terpolymers of acrylic acid, methacrylic acid, maleic acid and aspartic acid. Furthermore the chemical deposit control agents can be based on organic phosphonates and their derivatives, as well as on polyphosphates.

The dosage of these biocides and chemical deposit control agents has to be accomplished very carefully and conservative because they are very expensive and pose a health hazard. It is thus necessary to distinguish between various types of deposits and to determine the thickness of respective deposits.

A method and a device for high precision measurement of a characteristic of a fouling or scaling deposit inside a fluid vessel is disclosed in the prior art document WO 2009/141 135 A1. An ultrasonic emission signal is emitted by an ultrasonic transducer towards a reflecting area inside the fluid vessel and a distance between the ultrasonic transducer and the reflecting area or between the ultrasonic transducer and a deposit onto the reflecting area is measured by means of evaluating the time-domain reflective signal of the reflecting area or of the deposit covering the reflecting area. The measured distance is compared to a reference distance which has been measured in an initial calibration measurement step without any deposits onto the reflecting area. The difference between the measured distance and the reference distance is a measure for the thickness of the deposition. A disadvantage of this method is that the real distance between the ultrasonic transducer and the reflective area changes e.g. with the temperature or the pressure inside the fluid vessel. Therefore, the current distance between the ultrasonic transducer and the reflective area at the time of measurement cannot accurately defined by a previously measured reference distance. Consequently, the measurement of the thickness of the deposits comprises an unknown offset depending on operational conditions, like pressure and temperature.

In order to distinguish between scale and fouling deposits the prior art document WO 2009/141 135 A1 further discloses a device comprising two different ultrasonic transducers, wherein each of the ultrasonic transducers cooperates with a separate reflecting area. The two reflecting areas are provided with different acoustic impedances. As scaling and fouling deposits have also different acoustic impedances, a comparison between the amplitude of the time-domain reflective signal measured by the one ultrasonic transducer and the amplitude of the time-domain reflective signal measured by the other ultrasonic transducer enables to distinguish between fouling and scaling deposits. A disadvantage of said device and method is that the device has to be provided with two different measuring sections which leads to higher equipment costs, increased installation space and further errors sources, because the operational conditions are not equal everywhere in the liquid-bearing system and rather depends on the exact position along a fluid pipe, for instance.

SUMMARY

It is therefore an object of the present invention to provide a method and a device for detecting and analyzing deposits in a reflecting area that allows to detect deposits and to distinguish between different kind of deposits with increased accuracy and lower dependency on operational conditions. Furthermore, a more cost-effective, compact and robust device should be provided.

The object of the present invention is achieved by a method for detecting and analyzing deposits on a reflecting area, in particular inside a liquid-bearing system, comprising the steps of: Emitting an ultrasonic emission signal towards the reflecting area by an ultrasonic transducer in a first step; Detecting an ultrasonic reflection signal obtained by reflection of the ultrasonic emission signal in the area of the reflecting area by detection means in a second step; Determining a distribution of the run time of the detected ultrasonic reflection signal in response to a specified variable in a third step and analyzing the distribution in a fourth step in order to determine if deposits are deposited at least partially onto the reflecting area.

It is herewith advantageously possible to easily and reliably determine if deposits are deposited onto the reflecting area by analyzing the distribution of the run time in response to the specified variable. Furthermore, it can be distinguished between different kind of deposits, like e.g. scaling or fouling deposits, if the presence of deposits are detected. This is possible because it was found that the characteristic of the run time signal plotted against the variable (referred to as the distribution) varies in a measurable manner with the thickness and the kind of the deposits. Furthermore, the characteristic of the distribution depends on the extent of coverage by the deposits, so that even the rate of coverage of the reflecting area by the layer of deposits can be determined by analyzing the position and the shape of the distribution. It can be determined if the reflecting area is covered only partially or completely by the layer of deposits, for instance. Preferably, the distribution is analyzed in the fourth step whether the distribution comprises a stationary point, an inflection point, a break point, a pole and/or a discontinuity. In particular, also the position of the stationary point, the inflection point, the break point, the pole and/or the discontinuity is determined in the fourth step. According to another embodiment, the position, the gradient and/or the curvature of the distribution is analyzed in the fourth step. Advantageously, the form of the distribution comprises information about the nature of the deposits onto the reflecting area, like kind of depositions, thickness, coverage and the like. These information can be evaluated simply by determining the characteristics and in particular the significant mathematical conditions of the distribution. The specified variable comprises preferably emission parameters of the ultrasonic transducer, detecting parameters of the detection means and/or analyzing parameters of the analyzing unit, which are modified in the fourth step.

The above mentioned object of the present invention is furthermore achieved by a method for detecting and analyzing deposits in a reflecting area, in particular inside a liquid-bearing system, comprising the steps of: Emitting an ultrasonic emission signal towards the reflecting area by an ultrasonic transducer in a first step, detecting an ultrasonic reflection signal obtained by reflection of the ultrasonic emission signal in the reflecting area by detection means in a second step and analyzing whether the detected ultrasonic reflection signal comprises different run times by an analyzing unit in a third step in order to determine if fouling deposits and/or scaling deposits are deposited onto the reflecting area. This method is either another subject of the present invention or a preferred embodiment of the present invention.

According to the present invention, it is thereby advantageously possible to distinguish between fouling and scaling deposits without using two separate measuring sections or without necessarily performing calibrating measurements for determining a reference distance. The acoustic impedance of fouling deposits is substantially lower compared to the acoustic impedance of scaling deposits. If the reflecting area is covered by an accumulation of fouling deposits a small portion of the ultrasonic transmission signal is reflected by the fouling deposits, wherein the main part of the ultrasonic transmission signal is reflected by the reflecting area which is made of metal, for instance. Consequently, the detected ultrasonic reflection signal comprises a first peak with lower amplitude occurring from the reflection of the ultrasonic emission signal at the fouling deposit and a second peak with a higher amplitude occurring from the reflection of the ultrasonic emission signal at a further reflection surface in the reflecting area, e.g. the inner surface of the wall of an liquid pipe or container of the liquid-bearing system. The first peak is time-defined upstream to the second peak because the distance between the detecting means and the reflecting surface of the fouling deposits (first distance) is smaller than the distance between the detecting means and the reflection surface (second distance). Consequently, the run time of the first peak (in particular the first rising edge of the ultrasonic reflection signal) is shorter than the run time of the second peak (in particular the second rising edge of the ultrasonic reflection signal) because both peaks occurred from the same first edge of the ultrasonic emission signal. This means that the detected ultrasonic reflection signal comprises at least two different run times. If the reflecting area is covered, by contrast, with scaling deposits the ultrasonic emission signal is reflected substantially only at the reflecting surface of the scaling deposits. In this case, a second peak occurring from a reflection of the ultrasonic emission signal at the further reflection surface cannot be measured so that the detected ultrasonic reflection signal comprises only one run time which corresponds to the first distance between the detecting means and the reflecting surface of the scaling deposits.

In particular, the wording "deposits" in the sense of the present inventions stands for any kind of organic or inorganic contaminants and deposits that occurs in liquid-bearing systems, e.g. pipes or containers. Suchlike deposits occur e.g. in the form of films (also called "fouling"). These are formed primarily in aqueous systems at the interface with a solid phase. In case of micro-organisms caused films, they consist of a slimy layer in which micro-organisms (e.g. bacteria, algae, fungi, and protozoa) are embedded. As a rule, these films contain, other than the micro-organisms, primarily water and extra-cellular polymeric substances exuded by the micro-organisms which, in conjunction with the water, form hydro-gels and contain other nutrients or substances. Often, particles are included in the resulting slimy matrix that is found in the aqueous medium adjacent the interface. The films which occurs e.g. in papermaking plant are characterized by the fact that it contains a high proportion of fibers, fine substances, and inorganic pigments that are bound by the organic matrix. Such films typically are accompanied by protective exopolysaccharides ("slime", EPS) of microbiological sources and occur at the interface of these equipment surfaces and process water streams. Additionally, inorganic contaminants, such as calcium carbonate ("scale") and organic contaminants often deposit on such surfaces. These organic contaminants are typically known as "pitch" (e.g., resins from wood) and "stickies" (e.g., glues, adhesives, tape, and wax particles).

Preferably, the detected ultrasonic reflection signal is analyzed in the third step whether the amplitude of the first peak is substantially smaller than the amplitude of the second peak. If so, it could be concluded that the first and the second peak occurs from the same first peak in the ultrasonic emission signal, so that the corresponding run times of the first and the second peak are different. Preferably, also the difference between the two run times is determined (when the fouling deposits are identified) because the difference in the run times is a measure for the thickness of the layer of fouling deposit. The thickness of the fouling deposit can be calculated by multiplying the time difference with the speed of sound in water (similar to the speed of sound in the fouling deposit), for instance. Advantageously, the thickness of the fouling deposit can be calculated without any foregoing calibration measurements and without any use of reference values.

According to a preferred embodiment of the present invention, a distribution of the run time of the detected ultrasonic reflection signal is determined in the third step and the distribution is analyzed whether the distribution comprises a discontinuity in a fourth step.

It is herewith advantageously possible to precisely detect the differences in the run time between the first and the second peak in the detected ultrasonic reflection signal in a comparatively simple and reliable manner. Preferably, at least one adjusting parameter influencing the run time of the detected ultrasonic reflection signal is adjusted and the distribution of the run time in dependency of the adjusted parameter is monitored. If a discontinuity in the distribution is detected, it can advantageously be concluded that a changeover from the small peak to the higher peak or vice versa has been detected (as mentioned above, the small peak and the higher peak occur from the same peak of the ultrasonic emission signal), because the small peak is time-defined upstream to the higher peak. The presence of the discontinuity indicates that a fouling deposit covers the reflecting area. If accumulation of scaling is deposited onto the reflecting area, a suchlike discontinuity in the distribution does not occur. The parameters to be modified in order to find the discontinuity in the distribution in the fourth step are preferably emission parameters of the ultrasonic transducer, detecting parameters of the detection means and/or analyzing parameters of the analyzing unit (also referred to as the specified variable). Preferably, the position and/or the shape of the discontinuity in the distribution is determined in a fifth step in order to determine the scale of the fouling deposits onto the reflecting area in the fourth step when the discontinuity is detected in the fourth step. The position and the shape of the discontinuity is a measure for the extent of coverage by the deposits, so that it can advantageously be determined whether the reflecting area is covered only partially or completely by the layer of deposits, for instance.

According to a particularly preferred embodiment of the present invention, the detected ultrasonic reflection signal is amplified by an amplifier of the analyzing unit in the third step, wherein the gain of the amplifier is adjusted during the fourth step in order to find the discontinuity, preferably the gain is successively increased at least until the discontinuity is detected. If the gain is set to a low value, the amplitude of the smaller first peak is below the lower measuring limit and therefore the run time of the detected ultrasonic reflection signal (defined e.g. by the first rising edge of the incoming ultrasonic reflection signal) is determined by the higher peak (second peak) deriving from the reflection of the ultrasonic emission signal at the reflecting area. If the gain is increased successively, at some point comes the moment when the amplitude of the smaller peak (first peak deriving from the reflection of the ultrasonic emission signal at the surface of the fouling deposits onto the reflecting area) reaches the lower measuring limit (defined e.g. by a threshold of the detecting means or the analyzing unit). At this moment the run time of the detected ultrasonic reflection signal is determined by the earlier smaller peak and therefore the run time jumps to a shorter time value and the distribution of the detected ultrasonic reflection signal against the gain of the amplifier comprises discontinuity in the form of a step. If the reflecting area is covered by scaling deposits the distribution does not comprise a suchlike discontinuity as the ultrasonic reflection signal derives mainly from reflection at the surface of the scaling deposits. In this case, the distribution has no upstream peak with significantly lower amplitude.

According to another particularly preferred embodiment of the present invention, the run time is determined in dependency of a time of detection of the detected ultrasonic reflection signal in the third step, wherein the time of detection is determined by the time at which the detected ultrasonic reflection signal exceeds a certain threshold value, wherein the threshold value is adjusted during the fourth step in order to find the discontinuity, preferably the threshold value is successively decreased at least until the discontinuity is detected. It is herewith advantageously possible to search for the discontinuity in the distribution without adjusting the gain of the amplifier as the adjustment of the threshold value has, in principle, the same effect. It is at least conceivable that both the gain and the threshold value are adjusted.

According to another particularly preferred embodiment of the present invention, the ultrasonic emission signal is emitted by the ultrasonic transducer with a certain output power in the first step, wherein the output power is increased during the fourth step in order to find the discontinuity, preferably the output power is successively increased at least until the discontinuity is detected. It is herewith advantageously possible to search for the discontinuity in the distribution without adjusting the gain of the amplifier or the threshold value as the adjustment of the output power has a similar effect. Preferably, the output power and the gain and/or the threshold value are adjusted.

According to the present invention, it is preferred that a time offset in the distribution in the area of the discontinuity is determined in a fifth step in order to determine a thickness of the fouling deposits in a sixth step when the discontinuity is detected in the fourth step. Preferably, the thickness of the fouling deposits is calculated or at least estimated by multiplying the time offset with an acoustic speed value. The acoustic speed values corresponds to the speed of sound in water in order to only estimate the thickness as the speed of sound in water is similar to the speed of sound in fouling. Alternatively, a value for the speed of sound in fouling a accurately measured in prior reference measurements, in particular for certain temperatures. In this case, the acoustic speed value represents the accurate speed of sound in fouling in order to precisely calculate the thickness of the fouling deposits. Preferably, different acoustic speed values are provided for different temperatures, so that the thickness is determined by multiplying the time offset with an acoustic speed value in dependency of the actual temperature in order to eliminate inaccuracies deriving from temperature variations. Advantageously, the thickness can be quantified even if the operational conditions, like e.g. temperature and/or pressure, may vary.

According to another preferred embodiment of the present invention, the discontinuity in the distribution is detected by modifying the emission parameters, the detecting parameters and/or the analyzing parameters in a first substep of the fourth step, wherein a limited interval in the course of the distribution in which the discontinuity is located is determined in a second substep of the fourth step and wherein the emission parameters, the detecting parameters and/or the analyzing parameters are modified again only within the limited interval in a third substep of the fourth step, preferably only the limited interval is analyzed in order to determine the time offset in the fifth step. It is herewith advantageously possible to reduce the time consumption, so that short-term changes e.g. in the temperature of the liquid can be taken into account during the measurements. In the first substep, a comparatively rough and quick analysis is performed only to determine whether the distribution comprises a discontinuity or not. For this, the emission parameters, the detecting parameters and/or the analyzing parameters are modified in larger steps. If a discontinuity is detected, the interval in which the discontinuity is located will be determined in the second substep. The advantage of this approach is that only this limited interval has to be precisely analyzed further in the third substep instead of analyzing the whole distribution. Consequently, the emission parameters, the detecting parameters and/or the analyzing parameters can be modified within the interval with smaller steps, so that accurate measurements of the discontinuity are possible in a comparatively short time. In particular, the discontinuity can be located and quantified accurately without spending too much time with measurements in areas of the whole distribution (e.g. the peripheral regions of the distribution) where the discontinuity is certainly not located.

According to another preferred embodiment, the run time is compared with a reference value in a seventh step in order to determine a thickness of the scale deposits when different run times are not detected in the third step and/or when a discontinuity is not detected in the fourth step. Advantageously, the absence of different run times or a discontinuity in the distribution indicates that either scaling deposits are deposited onto the reflecting area or no deposits are located onto the reflecting area at all. A comparison of the one run time of the detected ultrasonic reflection signal with a reference value provides the possibility to recognize if an accumulation of scaling is covering the reflecting area. The reference value particularly corresponds to a run time for the ultrasonic signal when no deposits are located onto the reflecting area. The reference value is measured in calibration measurements in a zero step e.g. initially performed prior to the first operation of the industrial plant or immediately after installation of the reflecting area, the ultrasonic transducer, the detection means and/or the analyzing unit. If the one run time of the detected ultrasonic reflection signal is shorter than the reference value it can advantageously be concluded that the reflecting area is covered by scaling depositions. The difference between the determined run time and the reference value is a measure for the thickness of the layer of scaling deposits.

Preferably, the one run time of the detected ultrasonic reflection signal is compared with the reference value in dependency of the emission parameters, the detecting parameters, the analyzing parameters and/or a temperature parameter in the seventh step. It is herewith advantageously possible to choose a certain reference value in dependency of the actual operating conditions. If the fluid in the liquid-bearing system has a certain temperature and a certain pressure during the measurement, a corresponding reference value for these temperature and pressure values is compared with the measured run time. In particular multiple reference values for different emission parameters, detecting parameters, analyzing parameters, pressure parameters and/or temperature parameters are measured during the calibration measurements in the zero step.

Another subject of the present invention is a device for detecting and analyzing deposits in a reflecting area, in particular inside the liquid-bearing system, wherein the device comprises an ultrasonic transducer for emitting an ultrasonic emission signal towards the reflecting area, a detection means for detecting an ultrasonic reflection signal obtained by reflection of the ultrasonic emission signal in the area of the reflecting area and an analyzing unit for analyzing whether the detected ultrasonic reflection signal comprises different run times in order to determine if fouling deposits and/or scaling deposits are deposited on the reflecting area. Advantageously, the device is capable of carrying out the above mentioned method according to the present invention. It is therefore advantageously possible to distinguish between fouling or scaling deposits without the need for two different measuring sections. Consequently, the device according to the present inventions is more cost-effective, compact and robust compared to suchlike devices known from prior state of the art.

According to a preferred embodiment of the present invention, the analyzing unit is configured for determining a distribution of the run time of the detected ultrasonic reflection signal, wherein the analyzing unit is further configured to analyze whether the distribution comprises a discontinuity in order to determine if fouling deposits and/or scaling deposits are deposited in the reflecting area. The configuration of the analyzing unit enables a way to find different run times in the detected ultrasonic reflection signal which is comparatively simple to implement and does not require extensive hardware equipment, e.g. computing power, memory capacity, high frequency-techniques or the like. Preferably, the device is configured for modifying emission parameters of the ultrasonic transducer, detecting parameters of the detection means and/or analyzing parameters of the analyzing unit in order to find the discontinuity in the distribution. Alternatively or at the same time the analyzing unit comprises an amplifier for amplifying the detected ultrasonic reflection signal, wherein the analyzing unit is configured for successively increasing the gain of the amplifier in order to find the discontinuity in the distribution.

According to a preferred embodiment of the present invention, the analyzing unit is preferably configured for determining a time offset in the distribution in the area of the discontinuity and wherein the device comprises a multiplier for multiplying the time offset with the acoustic speed value in order to determine a thickness of the fouling deposits when a discontinuity is detected in the distribution. The acoustic speed value can be the speed of sound in water or a measured or estimated speed of sound in fouling, as described above. It is herewith advantageously possible to determine the thickness of the fouling deposits deposited onto the reflecting area without using two different measuring sections. Furthermore, initially performed calibration measurements are not necessarily needed.

According to another preferred embodiment of the present invention, the device comprises a reference value memory for storing at least one reference value measured in initially performed calibrating measurements and a comparator for comparing the run time with the reference value in order to determine a thickness of the scaling deposits when a discontinuity is not detected in the distribution. It is herewith advantageously possible to determine the thickness of the scaling deposits deposited onto the reflecting area According to a particularly preferred embodiment of the present invention, the reflecting area is a part of a wall of a fluid pipe or fluid container of the liquid-bearing system. In this embodiment the device is at least partially integrated into a fluid container for storing the liquid or into a fluid pipe for conducting the liquid. The liquid is preferably an aqueous fluid. The ultrasonic transducer is e.g. integrated into a first wall of the liquid pipe or liquid container, wherein the reflecting area is provided by a second wall of the fluid pipe or liquid container. The first wall and the second wall are located opposite to each other. In particular, the device is permanently installed into a wall of the liquid pipe or liquid container, so that a permanent and continuous monitoring of the scaling and fouling deposits can be accomplished.

In an alternative particularly preferred embodiment of the present invention, the device comprises a holding means protruding from the device itself or a wall of the fluid pipe of the water bearing system into the interior of the fluid pipe, wherein the reflecting area is a part of the holding means provided spaced apart from the ultrasonic transducer. It is herewith advantageously possible that the whole device is mounted only at one side wall of the fluid pipe or the fluid container.

In a further alternative particularly preferred embodiment of the present invention, the reflecting area is a part of an interchangeable sample carrier which is insertable into the liquid-bearing system and into the device. In this case, the device is separated from the liquid-bearing system. It is herewith advantageously possible that only the sample carrier has to be located at least temporarily inside of the liquid-bearing system, e.g. the fluid container for storing liquids or the pipe for conducting the fluid. In order to detect and analyze fouling and scaling deposits in the liquid-bearing system, the sample carrier is removed from the liquid-bearing system and inserted into the device only for the duration of the measurements. It is herewith advantageously possible that the device is provided as a portable handheld device. Furthermore, the device can be used for controlling multiple sample carriers temporarily located at many different places in one or more industrial plants.

Preferably, the device comprises a temperature sensor. It is also conceivable that a value representing the temperature of the liquid which is measured by means of a temperature sensor is transmitted by the communication interface.

For further embodiments and details of the method and the device according to the present invention, a reference is made to the disclosure of WO 2009/141 135 A1 which is incorporated herewith by reference.

Preferably, the device comprises a communication network interface for transmission of measurement data and/or analysis data via a communication network. The measurement data and/or analysis data can be transferred, in particular hardwired or wireless, via the communication network, e.g. the internet, a telephone network, a mobile communication network or the like, to a central memory, a central processing unit, a pump or a valve for leading an appropriate amount of biocides and/or chemical deposit control agents, based e.g. on homopolymers, copolymers and terpolymers of acrylic acid, methacrylic acid, maleic acid and aspartic acid or based on organic polyphosphates or phosphonates and their derivatives, into the liquid-bearing system.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Figure 1:
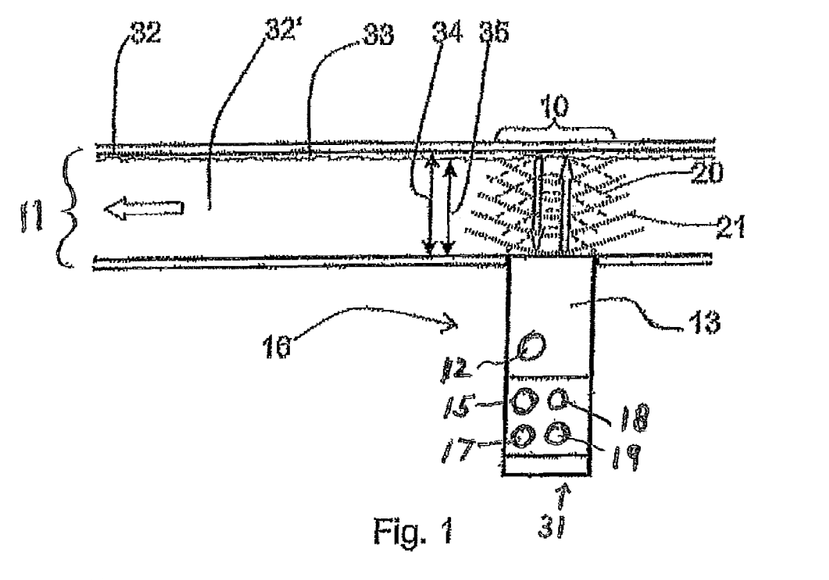
FIG. 1 illustrates schematically a device and a method for detecting and analyzing deposits according to an exemplary first embodiment of the present invention.

In FIG. 1, a device 16 for detecting and analyzing fouling and/or scaling deposits 33 inside a liquid-bearing system 11 according to an exemplary first embodiment of the present invention is shown. The device 16 comprises an ultrasonic transducer 12, a detection means 13 and an analyzing unit 14. In the present example, the liquid-bearing system 11 comprises a fluid pipe 32 for conducting a liquid medium 32', e.g. in a refrigerating plant, a pulp making plant or a paper making plant. The device 16 is integrated into a wall of the fluid pipe 32. An ultrasonic emission signal 20 is emitted by the ultrasonic transducer 12 towards a reflecting area 10. As an example, the reflecting area 10 is formed by a portion of the inner side wall of the fluid pipe 32. The ultrasonic transducer 12 and the reflecting area 10 are located on opposite sides of the fluid pipe 32 facing each other. The ultrasonic emission signal 20 comprises preferably multiple one after the other emitted discrete wave packets.

In order to detect and analyze fouling and/or scaling deposits 33 accumulated in the reflecting area 10 onto the inner walls of the fluid pipe 32, a ultrasonic reflection signal 21 occurred through a reflection of the ultrasonic emission signal 20 in the reflecting area 10 is detected by the detecting means 13. If there are no deposits 33 in the reflecting area 10 at all, the ultrasonic emission signal 20 is reflected by the surface of the inner wall of the fluid pipe 32. In this case, the ultrasonic reflection 21 traveled twice the distance (second distance 34) between the ultrasonic transducer 12 and the surface of the inner wall. The detected ultrasonic reflection signal 21 required a certain run time 22 for this distance. If there are fouling deposits 33 deposited on the inner wall of the fluid pipe 32 and inside of the reflecting area 10, the ultrasonic emission signal 20 is reflected partially by the fouling deposits 33 and mainly by the surface of the inner wall of the fluid pipe 32, because fouling deposits 33 have only low acoustic impedances. If there are scaling deposits 33 deposited on the inner wall of the fluid pipe 32 and inside of the reflecting area 10, the ultrasonic emission signal 20 is reflected by the surface of the scaling deposits 33 because scaling deposits 33 provide high acoustic impedances. Basically, it can be said that If at least a part of the ultrasonic emission signal 20 is reflected by the surface of the deposits 33, at least the corresponding part of the detected ultrasonic reflection signal 21 traveled twice the shorter distance (first distance 35 is smaller than the second distance 34) between the ultrasonic transducer 12 and the surface of the deposits 33. The corresponding detected ultrasonic reflection signal 21 requires therefore a shorter run time 22.

The detected ultrasonic reflection signal 21 is analyzed by the analyzing unit 14. For this purpose, the detected ultrasonic reflection signal 21 is amplified by an amplifier 15 of the analyzing unit 14. The analyzing unit 14 analyzes the amplified ultrasonic reflection signal 21 directly or indirectly whether the ultrasonic reflection signal 21 comprises two different run times 22. If e.g. the first rising edge of the emitted ultrasonic emission signal 20 is reflected partially at the surface of fouling deposits, e.g. a biofilm, located in the reflecting area 10 and mainly at the surface of the inner wall of the fluid pipe 32, the detected ultrasonic reflection signal 21 comprises a small first peak 40 deriving from reflection at the surface of the biofilm and a higher second peak 41 deriving from reflection at the inner wall (illustrated in detail in FIG. 2). Both, the first peak 40 and the second peak 41 have their origin in the same flange of the ultrasonic emission signal 20. The time lag 42 between the first peak 40 and the second peak 41 derives only because of different places of reflection, the surface of the biofilms on the one hand and the surface of the inner wall on the other hand. Consequently, the detected ultrasonic reflection signal 21 comprises two different run times 22, if a biofilm is deposited onto the inner wall. In other words, if two different run times 22 can be monitored it can be concluded that the reflecting area 10 is covered with fouling deposits 33.

Figure 2:
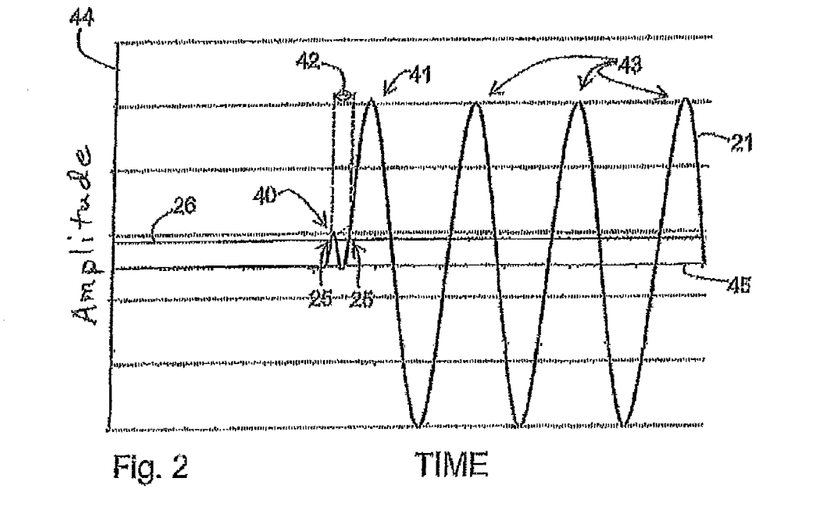
FIG. 2 illustrates schematically the shape of a detected ultrasonic reflection signal in a method for detecting and analyzing deposits according to the first embodiment of the present invention.

The amplitude of the first peak 40 is significantly lower than the amplitude of the second peak 41, because the acoustic impedance of the biofilms is lower than the acoustic impedance of the wall material, e.g. metal or plastic. It is herewith advantageously possible to distinguish between the first peek 40 derived from a biofilm and the "first" peak of the wave packet reflected at the inner wall (which is only the second peak 41 when a biofilm is covering the reflecting area 10). The frequency of the ultrasonic emission signal 20 is preferably set in such a manner that the time lag 42 between the first and the second peak 40, 41 can be resolved. In other words: The frequency of the ultrasonic emission signal 20 has to be high enough that the first peak 40 is not superimposed by the second peak 41. The width of the time lag 42 is defined by the actual distance between the surface of the biofilm on the one hand and the inner wall on the other hand. The speed of sound in biofilm is similar to the well known speed of sound in water. Consequently, the thickness of the detected biofilm can be calculated by multiplying the time lag 42 with the speed of sound in water by means of a multiplier 17 of the analyzing unit 14.

If a layer of fouling deposits 33 is indicated and in particular the thickness of the layer is determined, the analyzing unit 14 preferably generates a corresponding control signal initiating appropriate countermeasures, like adding biocides into the liquid medium 32' and into the fluid pipe 33. Preferably, the control signal depends on the determined thickness of the fouling deposits 33 in order to initiate a higher concentration of biocide in the liquid medium 32', if a thicker layer of fouling deposits 33 are determined, and a lower concentration of biocide, if the layer of fouling deposits 33 is thinner. It is conceivable that one or more pumps (not shown) are controlled directly by the control signal for pumping an appropriate amount of biocide into the liquid medium 32'. Alternatively, one or more valves (not shown) are controlled by the control signal for leading a corresponding amount of biocide into the liquid medium 32. Preferably, the device 16 comprises a communication network interface 31 transmitting the control signal and/or the measured data via a communications network, e.g. for recording, monitoring, controlling or maintenance purposes.

If the analyzing unit 14 does riot detect two different run times 22 in the detected ultrasonic reflection signal 21, it can be concluded that the inner wall in the reflecting area 10 is not covered by deposits 33 at all or that scaling deposits 33 are deposited onto the inner wall. In this case, a second run time 22 does not occur because the ultrasonic emission signal 20 is reflected almost completely by the exposed inner wall or by the surface of the layer of scaling deposits 33 because scaling deposits have comparatively high acoustic impedance. Consequently, a reflection of the same edge of the ultrasonic emission signal 20 at the inner wall as well as at the surface of the scaling deposits 33 is not measurable. In order to analyze whether scaling deposits 33 are accumulated onto the inner wall or not, the one run time 22 of the detected ultrasonic reflection signal 21 is determined by the analyzing unit 14 and the one run time 22 is subsequently compared with a reference value by a comparator 19 of the analyzing unit 14. The comparator 19 retrieves the reference value e.g. from a reference value memory 18 of the device 16. The reference value represents the run time 22 of an ultrasonic signal emitted by the ultrasonic transducer 12, reflected by the inner wall in the reflection area 10 and detected by the detections means 13, whereby the inner wall is not covered with any deposits 33 at all. In order to determine this reference value, initial calibrating measurements are performed, e.g. immediately after a first start-up of the plant or the pipe, after the liquid medium 32' is filled into the liquid-bearing system 11 or after installation of the device 16. If the determined run time 22 is smaller than the reference value, it can be concluded that the detected ultrasonic reflection signal 21 is reflected by the surface of the scaling deposits 33. In this case, the time difference between the run time 22 and the reference value is a measure for the thickness of the scaling deposits 33. The thickness of the detected layer of scaling deposits 33 can directly be calculated by multiplying the time difference with the speed of sound in water by means of a multiplier 17.

As described above, the method and the device 16 allows to distinguish between fouling deposits on the one hand and scaling deposits on the other hand. Fouling deposits are organic deposits which often occur in the form of biofilms in aqueous systems, wherein such biofilms substantially consist of micro-organisms, e.g. bacteria, algae, fungi and protozoa. Contrary thereto, scale depositions occur from inorganic matter that have been identified include e.g. complexes of calcium (carbonate, oxalate, sulfate, silicates), aluminum (silicates, hydroxides, phosphates), barium sulfate, radioactive radium sulfate, and silicates of magnesium.

As already indicated above, FIG. 2 schematically illustrates the shape of the detected ultrasonic reflection signal 21 in a method for detecting and analyzing fouling and/or scaling deposits performed by the device 16 (exemplary illustrated in FIG. 1). In the diagram of FIG. 2, the amplitude of the detected ultrasonic reflection signal 21 is plotted against time 25 in a case where the reflective area 10 is covered by fouling deposits 33. Furthermore, a threshold value 26 of the analyzing unit 14 is shown in the diagram defining a lower threshold from which a peak in the detected ultrasonic reflection signal 21 is taken into account. If a rising flange of the incoming ultrasonic reflection signal 21 exceeds the threshold value 26, a time of detection 25 for the corresponding flange is determined and a run time 22 for the detected ultrasonic reflection signal 21 can be calculated from the time difference between the time of detection 25 and the time of emitting the ultrasonic emission signal 20, whereby in particular the time of emitting the peak which initiates the corresponding peak in the reflection signal 21 is used for determined the run time 22.

In FIG. 2, it is shown that the first peak 40 which has a small amplitude due to reflection at the surface of the biofilm is time-defined upstream to the second peak 41, wherein the second peak 41 has a higher amplitude occurring from reflection at the inner wall of the fluid pipe 32. The presence of the smaller first peak 40 indicates that fouling deposits 33 are deposited on the reflection area 10, wherein the time lag 42 between the first peak 40 and the second peak 41 is a measure for the thickness of the fouling deposits 33. In order to detect the presence of the first peak 40, the analyzing unit 14 directly or indirectly analyzes whether the detected ultrasonic reflection signal 21 comprises two different run times 22, as described above. The second peak 41 is followed by several further peaks 43 originating from further peaks in the wave packet of the emitted ultrasonic emission signal 20 (all further peaks 43 have substantially the same run time 22 as the second peak 41). For the person skilled in the art it is clear that the first peak 40 could also be the other way round, so that the first peak 40 is directed downwards. In reality, the signals are overdriven by the gain of the amplifier so that there is no measurable difference in the amplitude between the first and the second peaks 40, 41. The first and the second peaks 40, 41 are rather merged into each other, The method for finding and analyzing different run times 22 in the detected ultrasonic reflection signal 22 in order to distinguish between fouling deposits 33 and scaling deposits 33 can be optimized by analyzing a distribution of the ultrasonic reflection signal 22 whether the distribution 24 comprises a discontinuity 24 or not. There are several possibilities that a fouling deposit 33 is not detected because the first peak 40 is below the threshold value 26 and therefore not taken into account, although the first peak 40 actually exists. This may e.g. occur if the output power of the ultrasonic transducer 12 or the gain of the amplifier 15 is too low or if the threshold value is set too high. Other causes may be that the smaller peak 40 cannot be resolved because the first peak 40 is superimposed by the second peak 41. To avoid this, at least one parameter, e.g. the output power (also referred to as emission parameter), the gain of the amplifier (also referred to as detecting parameter) and/or the threshold value 26 (also referred to as analyzing parameter), is adjusted during the measurements. Preferably, the gain starts from a low value and is successively increased.

Figure 3:
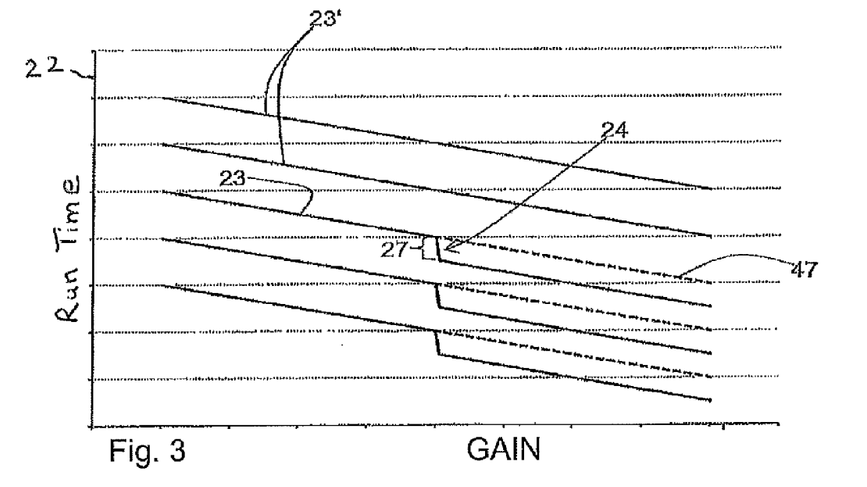
FIG. 3 illustrates schematically the distribution of the run time of different detected ultrasonic reflection signals in a method for detecting and analyzing deposits according to the first embodiment of the present invention.

The distribution 23 of the resulting ultrasonic reflection signal 21 in dependency of the changing gain is illustrated in FIG. 3. The run time 22 is calculated from the time difference between emitting the ultrasonic emission signal 20 and detecting the first edge of the ultrasonic reflection signal 21 (at the intersection between the first edge and the threshold value 26, also referred to as time of detection 25). At the beginning, the first peak 40 does not exceed the threshold value 26 (cp. FIG. 2) and is therefore not taken into account. The run time 22 is defined by the time of detection 25 of the rising edge of the second peak 41. Due to the recently increased gain, the amplitude of the second peak 41 increases and therefore the rising edge of the second peak 41 becomes steeper. Consequently, the intersection point between the rising edge of the second peak 41 and the threshold value 26 moves successively to shorter run times 22. For this reason, the distribution 23 of the run time 22 of the detected ultrasonic reflection signal 21 falls linearly with increasing gain (cp. FIG. 3). At some point, the first peak 40 exceeds the threshold value 26 and from that point, the run time 22 is defined by the intersection between the rising flange of the first peak 40 and the threshold value 26. For that reason, the distribution 23 comprises a discontinuity 24 in the form of a sharp step. The presence of the discontinuity 24 indicates that fouling deposits 33 are deposited in the reflecting area 10. If scaling deposits 33 would be deposited in the reflecting area 10, the distribution 23 of the run time 22 would not comprises a suchlike discontinuity. Rather, the distribution 23 would remain continuous as illustrated by the dotted lines 47. A time offset 27 defined by the width of the step in the distribution 23 along the vertical axis is a measure for the distance between the surface of the fouling deposits 33 and the inner wall of the fluid pipe 32. Therefore, the thickness of the layer of fouling deposits can simply be calculated by multiplying the time offset 27 with the speed of sound in water (similar to the speed of sound in biofilms).

The diagram, illustrated in FIG. 3, comprises different distributions 24 of the run time 22 for different operational conditions in the liquid-bearing system 11. The different operational conditions, like temperature or pressure of the liquid fluid 32', influences the width of the fluid pipe 32, so that the first distance 35 between the ultrasonic transducer 12 and the inner wall in the reflecting area 10 changes and therefore the corresponding run times 22 are different, at least as long as the speed of sound in the liquid medium 32' remains constant. As a result, the different distributions 23 are parallel to each other and only shifted along the vertical axis. The two uppermost distributions 23' illustrates for clarification purposes only plots of the run time 22 against the increasing gain without fouling deposits 33 onto the reflecting area 10. These distributions 23' do not have any discontinuities 24. In order to distinguish whether the reflecting area 10 is covered by scaling deposits 33 or if the reflecting area 10 is not covered by deposits at all, the run time 22 for a certain gain and certain operational conditions has to be compared with a corresponding reference value measured with said gain and operational conditions. In this way, also the thickness of the scaling deposits 33 can be calculated by calculating the difference between the reference value and the recent run time 22 and multiplying the difference with the speed of sound in water.

Figure 4:
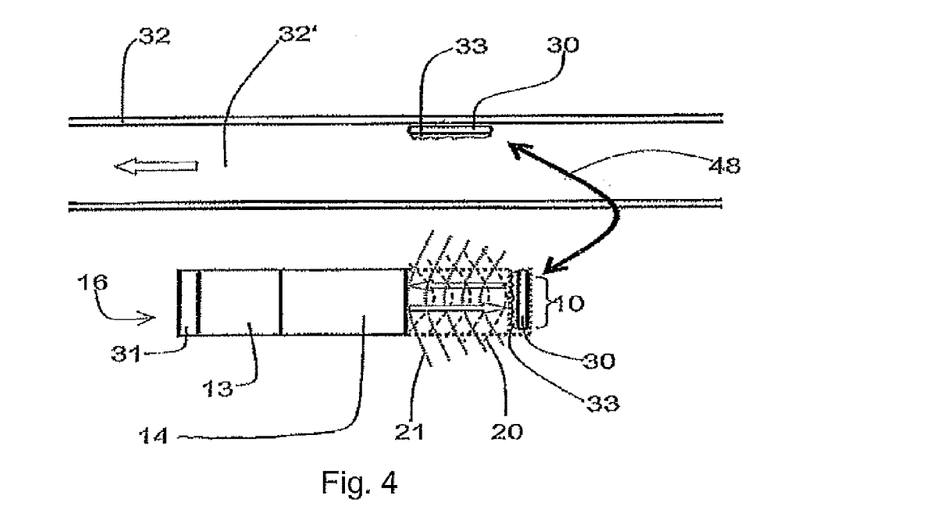
FIG. 4 illustrates schematically a device for detecting and analyzing deposits according to a second embodiment of the present invention.

In FIG. 4, a device 16 for detecting and analyzing fouling and/or scaling deposits 33 according to a second embodiment of the present invention is schematically illustrated. The device 16 according to the second embodiment works in principle in the same way as the device 16 according to the first embodiment illustrated in FIG. 1. The only difference is that the device 16 according to the second embodiment is not integrated into the liquid-bearing system 11. On the contrary, the device 16 can be provided as a portable handheld apparatus. The reflecting area 10 is formed by an interchangeable sample carrier 30. The sample carrier 30 is located temporarily inside the liquid-bearing system 11 whose walls should be monitored in consideration of potential fouling and/or scaling deposits 33. In order to detect and analyze a potential deposition 33 of scale or fouling, the sample carrier 30 is removed from the liquid-bearing system 11 and inserted into a corresponding slot of the portable device 16 (illustrated by double arrow 48). Subsequently, the above described method for detecting and analyzing scaling and/or fouling deposits 33 are performed in order to distinguish and to quantify fouling and/or scaling deposits 33 onto the sample carrier 30. In the present example, the surface of the sample carrier 30 works as the reflecting area 10 in the sense of the present invention. Preferably, the device 16 is used for controlling multiple sample carriers 30 (not shown) located at different places in one or more industrial plants. The communication network interface 31 comprises preferably a transmitter for hard-wired or wireless data transmission. It is also conceivable that a value representing the temperature of the liquid which is measured by means of a temperature sensor is transmitted by the communication interface.

Figure 5:
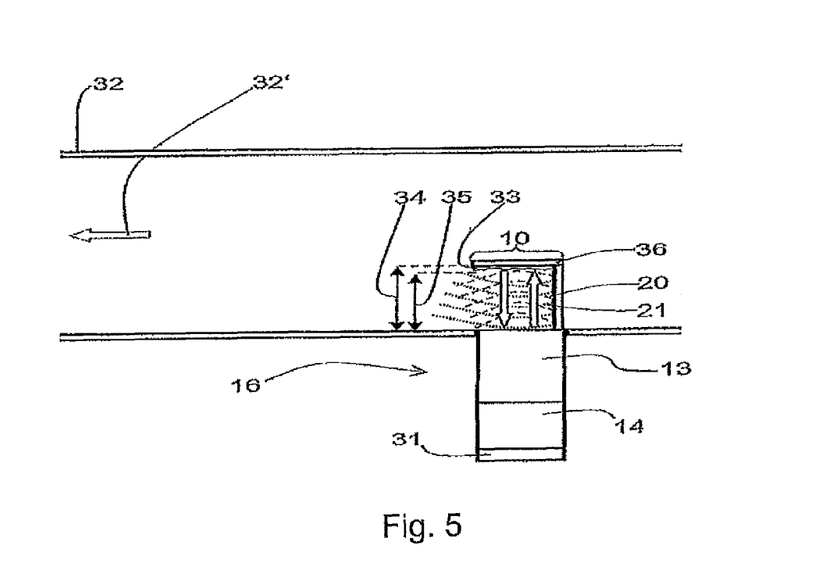
FIG. 5 illustrates schematically a device for detecting and analyzing deposits according to a third embodiment of the present invention.

In FIG. 5, a device 16 for detecting and analyzing fouling and/or scaling deposits 33 according to a third embodiment of the present invention is schematically illustrated. The device 16 according to the third embodiment works in principle in the same way as the device 16 according to the first embodiment illustrated in FIG. 1. The only difference is that the device 16 according to the second embodiment comprises a L-shaped holding means 36 protruding from a wall of the fluid pipe 32 of the water bearing system 11 into the interior of the fluid pipe 32. The reflecting area 10 is provided as a part of the L-shaped holding means 36, so that the reflecting area 10 is located spaced apart from the ultrasonic transducer 12.

Figure 6:
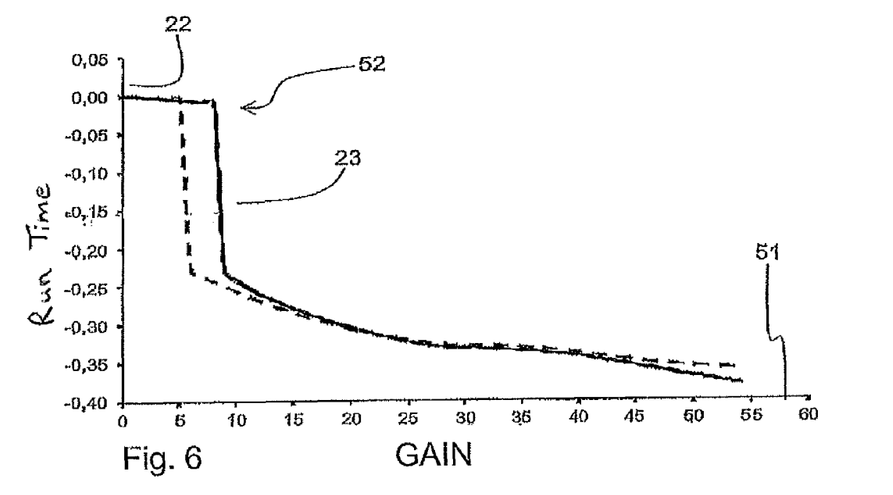
FIGS. 6, 7 and 8 illustrate different distributions of run times once with and once without deposits onto the reflecting area in each case according to further embodiments of the present invention.

In FIG. 6, a distribution 23 of the run times in a method for detecting and analyzing deposits 33 according to a further embodiment of the present invention is shown. The method according to the further embodiment is similar to the above mentioned methods, whereby the shape of the distribution 23 is analyzed by the analyzing unit 14 in order to detect deposits 33 onto the reflecting area 10 and if so, to determine the thickness and the scale of the layer of deposits 33 onto the reflecting area 10. In FIG. 6, the run time 22 (in microseconds) of the ultrasonic reflection signal 21 is plotted against the gain (in decibels) of the amplifier 15 (solid line) based on actual measurement data. The distribution 23 shows the course of the run time 22 in response to the increasing gain as the variable, when fouling deposits 33 (biofouling in the present example) are deposited onto the reflecting area 10. In the present example, the fouling deposits 33 are located not as a continuous layer covering the complete reflecting area 10, but rather as single islands of deposits 33 which are isolated from each other and which cover the reflecting area 10 only very partially.

Furthermore, a reference distribution 51 (dotted line) is illustrated for illustrative purposes only. The reference distribution 51 shows the course of the ultrasonic reflection signal 21 in response to the changing gain 46, if no deposits 33 are located in the reflecting area 10 at all.

It can be seen that the first break point 52 of the distribution 23 is shifted along the x-axis compared to the reference distribution 51. The first break point 52 is caused by reflection of the ultrasonic emission signal 20 at the metal surface of the reflection area 10. In the distribution 23, the first break point 52 is shifted to higher gain because the fouling deposits 33 onto the reflecting area 10 damp the ultrasonic reflection signal 21 reflected by the metal surface. Of course, the shift 52 could also be used as an indicator for the thickness of the fouling deposits 33. But in this case, the reference distribution 51 has to be monitored for the comparison with the distribution 23.

In the further course of the distribution 23, the distribution 23 and the reference distribution 51 diverge more and more, wherein the divergence starts at a gain of approximately 50 decibels. The distribution 23 does not have a sharp discontinuity or a further break point in this area because the fouling deposits 33 are located only sporadic over the reflecting area 10. But it can been seen from the distribution 23 that the presence of suchlike deposits 33 influences at least the gradient of the distribution 23.

Consequently, the presence of fouling deposits 33 formed as single isolated islands partially covering the reflecting area 10 can be detected only by analyzing the gradient of the distribution 23.

Figure 7:
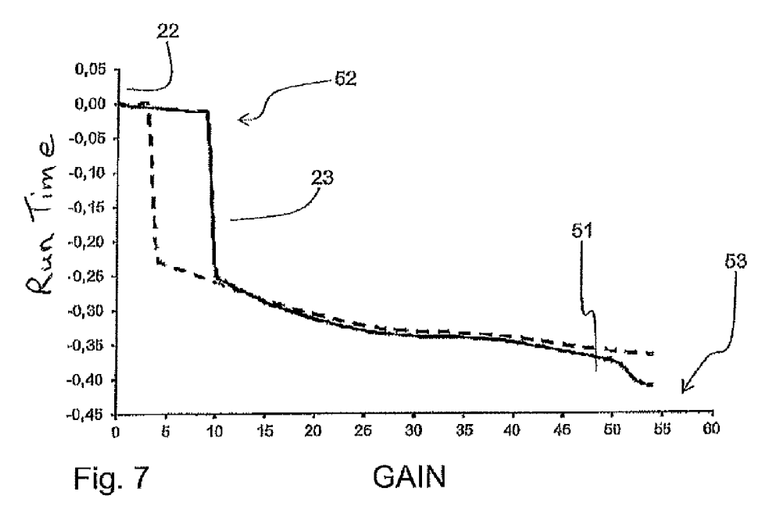

FIG. 7 shows a similar distribution 23 and reference distribution 51 of run times 22 in a method for detecting and analyzing deposits 33 according to a further embodiment of the present invention. Here, the run time 22 (in microseconds) of the ultrasonic reflection signal 21 is also plotted against the gain (in decibels) of the amplifier 15 (solid line) based on actual measurement data, whereby in the present example the reflecting area 10 is covered by a comparatively thick layer of fouling deposits 33 distributed in a more homogeneous manner. It can been seen that the distribution 23 comprises already a kind of a discontinuity in the form of a blurred second break point 53. The presence of the second break point 53 is an indicator for the presence of the more homogenous layer of fouling deposits 33 onto the reflecting area 10. The second break point 53 can be found by analyzing the distribution 23 whether it comprises an inflection point or a discontinuity or by analyzing the gradient and/or the curvature of the distribution 23.

Figure 8:
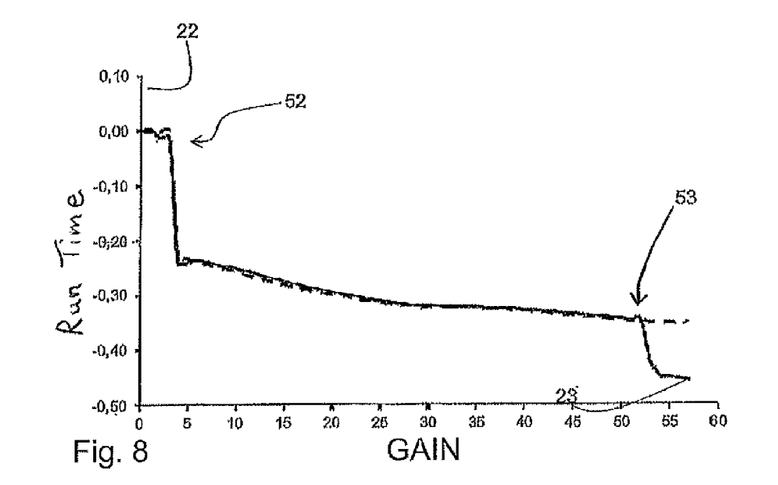

In FIG. 8, another example of a distribution 23 is shown. In this example, the reflecting area 10 is covered by a homogenous layer of fouling deposits 3. Accordingly, the distribution 23 can be seen clearly. The second break point 53 can e.g. be found by looking for a stationary point in the form of a local maximum in the distribution 23. The width of the discontinuity along the y-axis is an indirect s measure for the thickness of the layer of fouling deposits 33 (as described above).

REFERENCE SIGNS 10 reflecting area
11 liquid-bearing system
12 ultrasonic transducer
13 detection means
14 analyzing unit
15 amplifier
16 device
17 multiplier
18 reference value memory
19 comparator
20 ultrasonic emission signal
21 ultrasonic reflection signal
22 run time
23 distribution of the run time
24 discontinuity in the distribution of the run time
25 time of detection
26 threshold value
27 time offset
30 sample carrier
31 communication network interface
32' liquid medium
32 fluid pipe
33 scaling and/or fouling deposits
34 second distance
35 first distance
36 L-shaped holding means
40 first peak
41 second peak
42 time lag
43 following peaks
44 amplitude
45 time
50 variable
51 reference distribution
52 first break point
52 second breakpoint
54 local maximum

The invention claimed is:
1. A method for detecting and analyzing deposits on a reflecting area inside a liquid-bearing system, comprising the steps of:
  emitting an ultrasonic emission signal towards the reflecting area by an ultrasonic transducer in a first step;

detecting an ultrasonic reflection signal obtained by reflection of the ultrasonic emission signal in the area of the reflecting area by detection means in a second step;

determining a distribution of a run time of the detected ultrasonic reflection signal in response to a specified variable in a third step; wherein the run time is calculated from the time difference between the time of detection and the time of emitting the ultrasonic emission signal;

analyzing the distribution in a fourth step in order to determine if deposits are deposited at least partially onto the reflecting area.

2. The method according to claim 1, wherein the distribution is analyzed in the fourth step whether the distribution comprises a stationary point, an inflection point, a break point, a pole and/or a discontinuity.

3. The method according to claim 2, wherein the distribution is analyzed for the distributions position, gradient and/or curvature of the distribution and/or the position of the stationary point, the inflection point, the break point, the pole and/or a discontinuity is analyzed in the fourth step.

4. A method for detecting and analyzing deposits on a reflecting area according to claim 3, comprising the steps of:
emitting an ultrasonic emission signal towards the reflecting area by an ultrasonic transducer in a first step;
detecting an ultrasonic reflection signal obtained by reflection of the ultrasonic emission signal in the area of the reflecting area by detection means in a second step;
analyzing whether the detected ultrasonic reflection signal comprises different run times by an analyzing unit in a third step in order to determine if fouling and/or scaling deposits are deposited onto the reflecting area.

5. The method according to claim 4, wherein a distribution of the different run times of the detected ultrasonic reflection signal is determined in the third step and the distribution is analyzed whether the distribution comprises a discontinuity in a fourth step.

6. The method according to claim 5, wherein emission parameters of the ultrasonic transducer, detecting parameters of the detection means and/or analyzing parameters of the analyzing unit are modified in order to find the discontinuity in the distribution in the fourth step.

7. The method according to claim 6, wherein the detected ultrasonic reflection signal is amplified by an amplifier of the analyzing unit in the third step, wherein the gain of the amplifier is adjusted during the fourth step in order to find the discontinuity wherein the gain is successively increased at least until the discontinuity is detected.

8. The method according to claim 7, wherein the different run times are determined in dependency of a time of detection of the detected ultrasonic reflection signal in the third step, wherein the time of detection is determined by the time at which the detected ultrasonic reflection signal exceeds a threshold value, wherein the threshold value is adjusted during the fourth step in order to find the discontinuity wherein the threshold value is successively decreased at least until the discontinuity is detected.

9. The method according to claim 8, wherein the ultrasonic emission signal is emitted by the ultrasonic transducer with a output power in the first step, wherein the output power is increased during the fourth step in order to find the discontinuity, wherein the output power is successively increased at least until the discontinuity is detected.

10. The method according to claim 9, wherein a time offset in the distribution in the area of the discontinuity is determined in a fifth step in order to determine a thickness of the fouling deposits in a sixth step when the discontinuity is detected in the fourth step.

11. The method according to claim 6, wherein the discontinuity in the distribution is detected by modifying the emission parameters, the detecting parameters and/or the analyzing parameters in a first substep of the fourth step, wherein a limited interval in the course of the distribution in which the discontinuity is located is determined in a second substep of the fourth step and wherein the emission parameters, the detecting parameters and/or the analyzing parameters are modified again only within the limited interval in a third substep of the fourth step, wherein only the limited interval is analyzed in order to determine a time offset in the fifth step.

12. The method according to claim 11, wherein the thickness of the fouling deposits is determined by multiplying the time offset with an acoustic speed value in the sixth step, wherein the acoustic speed value represents the speed of sound in water or the speed of sound in fouling deposits.

13. The method according to claim 12, wherein a certain acoustic speed value is used in dependence of an actual temperature in the sixth step and/or wherein an acoustic speed value is determined by measuring and/or estimating a speed of sound in fouling deposits in prior reference measurements.

14. The method according to claim 1, wherein the run time is compared with a reference value in a seventh step in order to determine a thickness of the scale deposits when different run times are not detected in the third step and/or when a discontinuity is not detected in the fourth step.

15. A device for detecting and analyzing deposits in a reflecting area inside a liquid-bearing system, wherein the device-comprises an ultrasonic transducer for emitting an ultrasonic emission signal towards the reflecting area, a detection means for detecting an ultrasonic reflection signal obtained by reflection of the ultrasonic emission signal in the area of the reflecting area and an analyzing unit for determining a distribution of a run time of the detected ultrasonic reflection signal in response to a specified variable and for analyzing the distribution in order to determine if deposits are deposited at least partially onto the reflecting area; wherein the run time is calculated from the time difference between the time of detection 25 and the time of emitting the ultrasonic emission signal.

16. The device according to claim 15, wherein the device is configured for modifying emission parameters of the ultrasonic transducer, detecting parameters of the detection means and/or analyzing parameters of the analyzing unit as the variable in order to determine the distribution.

17. A device for detecting and analyzing deposits in a reflecting area inside a liquid-bearing system, wherein the device comprises an ultrasonic transducer for emitting an ultrasonic emission signal-towards the reflecting area, a detection means for detecting an ultrasonic reflection signal-obtained by reflection of the ultrasonic emission signal in the area of the reflecting area and an analyzing unit for analyzing whether the detected ultrasonic reflection signal comprises different run times in order to determine if fouling and/or scaling deposits are deposited onto the reflecting area; and wherein the analyzing unit is configured for determining a distribution of the run time of the detected ultrasonic reflection signal, wherein the analyzing unit is further configured to analyze whether the distribution comprises a discontinuity in order to determine if fouling deposits and/or scaling deposits are deposited in the reflecting area.

\* \* \* \* \*

UNITED STATES PATENT AND TRADEMARK OFFICE
CERTIFICATE OF CORRECTION

PATENT NO. : 9,587,935 B2  Page 1 of 1
APPLICATION NO. : 14/367262
DATED : March 7, 2017
INVENTOR(S) : Seida et al.

It is certified that error appears in the above-identified patent and that said Letters Patent is hereby corrected as shown below:

In (72) Inventors:
"Schultz, Bad Durrenbert (DE)"

Should read:
-- Schultz, Bad Durrenberg (DE) --

Signed and Sealed this
Sixth Day of June, 2017

Michelle K. Lee
*Director of the United States Patent and Trademark Office*